(12) United States Patent
Krumbiegel et al.

(10) Patent No.: US 6,169,915 B1
(45) Date of Patent: Jan. 2, 2001

(54) DEVICE FOR FASTENING OF SENSORS TO THE SURFACE OF THE SKIN AND A METHOD FOR DETECTING THE REMOVAL OF SENSORS FROM THE SURFACE OF THE SKIN

(75) Inventors: Peter Krumbiegel; Ulrike Rolle-Kampczyk, both of Leipzig (DE)

(73) Assignee: UFZ-Umweltforschungszentrum Leipzighalle GmbH, Leipzig (DE)

( * ) Notice: Under 35 U.S.C. 154(b), the term of this patent shall be extended for 0 days.

(21) Appl. No.: 09/117,709

(22) PCT Filed: Jan. 13, 1997

(86) PCT No.: PCT/EP97/00140

§ 371 Date: Nov. 4, 1998

§ 102(e) Date: Nov. 4, 1998

(87) PCT Pub. No.: WO97/28772

PCT Pub. Date: Aug. 14, 1997

(51) Int. Cl.[7] .............................................. A61B 5/04
(52) U.S. Cl. ........................ 600/372; 600/386; 600/391; 600/584
(58) Field of Search .................... 600/372, 382, 600/384, 386, 387, 391, 393, 346, 362, 573, 575, 584; 604/358

(56) References Cited

U.S. PATENT DOCUMENTS

| 3,631,617 | * | 1/1972 | Pekko . | |
| 4,515,162 | * | 5/1985 | Yamamoto et al. | 128/640 |
| 5,203,327 | * | 4/1993 | Schoendorfer et al. . | |
| 5,396,901 | * | 3/1995 | Phillips | 128/771 |
| 5,944,662 | * | 8/1999 | Schoendorfer | 600/362 |

FOREIGN PATENT DOCUMENTS

| 7628422 | * | 3/1978 | (DE) . |
| 4338466A1 | * | 5/1995 | (DE) . |

* cited by examiner

*Primary Examiner*—Michael Peffley
*Assistant Examiner*—David M. Ruddy
(74) *Attorney, Agent, or Firm*—Birch, Stewart, Kolasch & Birch, LLP

(57) ABSTRACT

The present invention relates to a device for attaching sensors to the surface of the skin comprising a basic plaster 3 and a detection plaster 4 which comprises a recess so that a hollow space 5 is provided between the basic plaster 3 and the detection plaster 4. The hollow space may contain a dye solution, solid matter, or odor marker which escapes during the unauthorized removal of the sensor by tearing open the hollow space 5.

13 Claims, 1 Drawing Sheet

DEVICE FOR FASTENING OF SENSORS TO THE SURFACE OF THE SKIN AND A METHOD FOR DETECTING THE REMOVAL OF SENSORS FROM THE SURFACE OF THE SKIN

This application claims the benefit under 35 U.S.C. §371 of prior PCT International Application No. PCT/EP97/00140 which has an International filing date of Jan. 13, 1997 which designated the United States of America, the entire contents of which are hereby incorporated by reference.

FIELD OF THE INVENTION

The present invention relates to a device for attaching sensors to the surface of the skin and includes a method for proving the removal of such sensors in order to find evidence for example for the unauthorised removal of a sensor from the human body.

DESCRIPTION OF THE BACKGROUND ART

Often there is a necessity to attach a sensor to the human body which for a longer period of time and without supervision records and/or transmits certain signals emerging from the human body (such as sounds, noises, temperature variations, fluid secretion) or signals of external effects onto the body (e.g. caused by pollutants, sound, heat, cold). Such sensors may be commercial ones which continuously or intermittently detect or record or transmit certain signals to be evaluated later. According to this invention, such sensors are for instance electrocardiogram recording and analysing devices, pulse sensing/evaluating devices (pulse watches) or blood pressure measuring devices or bronchitis-asthma sensors as described for instance in DE 43 38 466 A1.

Usually such sensors are fixedly attached to the skin by means of attachment devices such as fixation strips or sticking plaster made of a wide variety of materials so that they can remain on the body for several weeks without causing inconveniences in cleaning the body. Said attachment devices are commercially available in any shape whatsoever and are for instance sold by Messrs. ARBO®-GmbH. If said sensors are for instance of a circular shape, annular sticking plasters may be used to attach them. Irrespective of the shape of the particular sensor, the attachment is effected in all cases by tightly covering parts of the sensor or the complete sensor plus—without any gap—a skin area surrounding the sensor with the usual adhesive sticking devices, thus providing a close skin contact of the side of the sensor facing the surface of the skin and ensuring water tightness.

DE-GM 76 28 422 discloses for example a sticking device for applying a measuring sensor for functional diagnostic purposes essentially comprising an adhesive ring which is meant to securely prevent artefacts even due to extreme body movements.

In the course of the development in microelectronics and sensor technology, the sensors described are increasingly used as legal evidence for assessing certain stresses a person is exposed to. In such cases, abuse and fraud by the person concerned cannot be excluded as such a person may for instance remove the sensor from his/her body and either hand it over to a third person suffering from asthma or the like or—in case of a pollution sensor—deposit it at a highly polluted place other than the place where the person actually is. Shortly before the scheduled removal of the sensor by an official, the person to be investigated might re-attach the sensor to his/her own body.

Until now, reliable systems and methods for proving the unauthorised removal of sensors from the skin do not exist.

Theoretically conceivable methods, such as gene, sweat, or trace analysis as used by criminologists in some exceptional cases, would be too lavish and costly for the purpose according to the present invention and at the same time might bring about uncertain results. For example, U.S. Pat. No. 5,203,327 discloses a plaster for the non-invasive determination of analytes (e.g. drugs) in body fluids which is used to collect excreted fluid and in which the analytes are compound with specific immobilised bonding partners and visually indicated. The plaster may contain certain markers which indicate the removal of the plaster from the skin and any possible falsification of the analytes detected (e.g. by diluting with water). However, this technological solution is too costly and therefore inappropriate for the purpose according to the present invention.

Likewise, the known method of self-destruction of foil-like stickers when being peeled off from a rigid surface, like those being used as highway toll or price stickers, is useless for the plaster/skin system because the movement of the skin itself might cause the uncontrollable, quick tearing of the foil seams thus eliminating the required constant water tightness and solidity after a short period of time.

SUMMARY OF THE INVENTION

It is an object of the present invention to provide an attachment device for sensors to be attached to the surface of the skin, capable of proving a removal of the sensor from the body, and to provide a method for proving the removal of sensors from the surface of the skin.

This object is achieved by means of an attachment device 1 and by a proving method.

The attachment device represents a simple solution which can easily be implemented technologically for subsequently and reliably proving a removal of the sensor from the body of a person at whom certain signals pertaining to said person were meant to be recorded.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
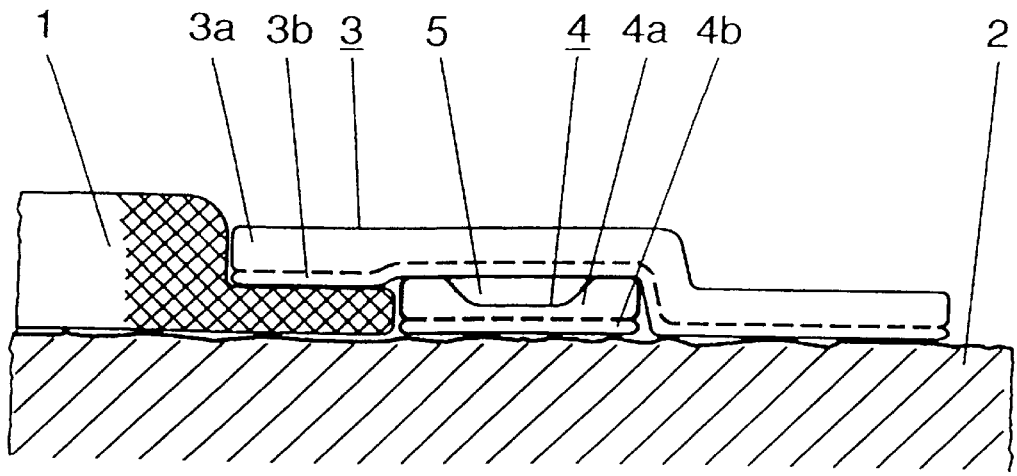
FIG. 1 shows a cross-sectional view of the attachment device in its adhering state.
Figure 2:
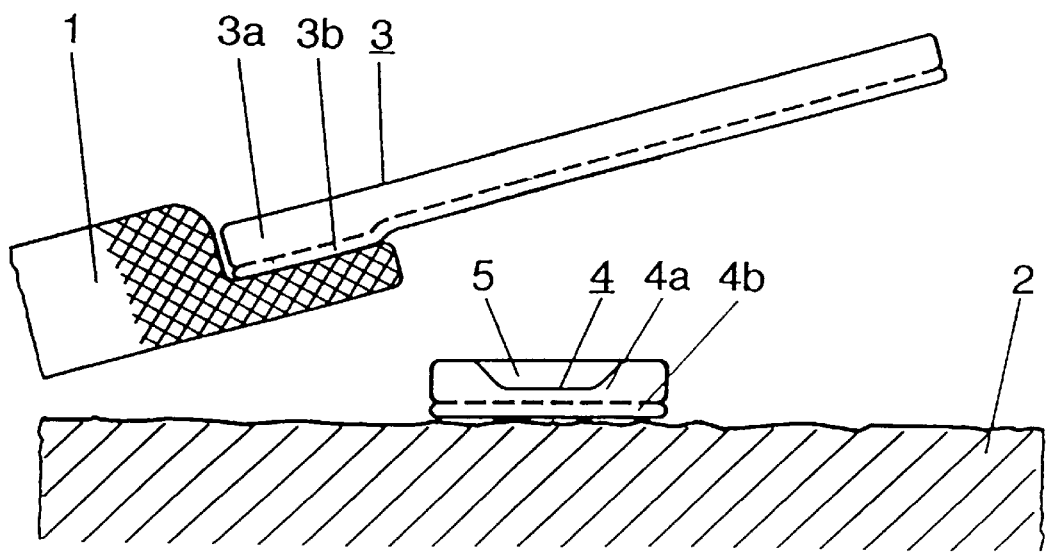
FIG. 2 shows a cross-sectional view of the attachment device after removal of the sensor from the skin.

Referring now to the drawings and with reference to FIG. 1, the attachment device according to the present invention is shown. This attachment device comprises a basic plaster 3 and a detection plaster 4 attached to the adhesive side 3b of the basic plaster, wherein said detection plaster 4 comprises a recess thus generating a hollow space 5 between said basic plaster 3 and said detection plaster 4, which hollow space will tear open due to the weak adhesion between said basic plaster 3 and said detection plaster 4 when the sensor is removed. A sensor 1 is provided adjacent the basic plaster 3. The basic plaster 3 has the adhesive layer 3*b* as well as a supporting layer 3*a*.

The attachment device according to the present invention uses such supporting materials as are usual for such attachment devices, such as foam supports, microporous supports, fabric supports. According to the present invention, the supporting layer 4*a* of said detection plaster can be formed of the same supporting material as the supporting layer of said basic plaster 3. Likewise, the adhesive layers of said basic and detection plasters 3*b*, 4*b* may comprise adhesive materials usually applied on such attachment devices. Thus, the adhesive layer 4*b* of said detection plaster may be of the same basic composition as the one of said basic plaster 3*b*, e.g. comprising a mixture of phthalate resin, polyvinyl ether and acrylate polymeride compound. In a preferred embodiment of the present invention, said supporting layer 4*a* of said detection plaster which provides its annular adhesion to said adhesive layer 3*b* of said basic plaster is formed of a relatively smooth material in order to minimise the adhesive strength between said basic and detection plasters. In a preferred embodiment, the adhesive strength between said basic and detection plasters is two to ten times less than the adhesive strength between said basic or said detection plaster and the skin.

In a preferred embodiment, said hollow space 5 of said detection plaster is filled with a fluid, a solid material or a gas during manufacturing of the attachment device according to the present invention, so that, at sticking together said basic plaster and said detection plaster, a touching or adhesive contact between said adhesive layer of said basic plaster and the inner area of said detection plaster is prevented. Preferably, the portion of said basic plaster which covers said hollow space may also be formed without an adhesive layer 3*b*.

If said adhesive layer 4*b* of said detection plaster has the same composition as that of said basic plaster, both adhesive layers have the same adhesive capability on the skin 2. In a preferred embodiment of the present invention, however, said adhesive layer 4*b* of said detection plaster has an adhesive strength which is two to five times greater than that of said basic plaster 3*b*. This can be achieved by using an increased portion of polyacrylate or by adding cyanoacrylate. In both cases the adhesive strength between said basic and detection plasters will be less than between said detection plaster or said basic plaster and the skin. Therefore, when said basic plaster is peeled off the skin, said detection plaster remains sticking to the skin while the hollow space 5 now torn open serves as proof for the removal of the sensor.

In another embodiment of the present invention, the portion of said basic plaster covering said hollow space 5 does not comprise an adhesive layer 3*b* while the supporting layer 3*a* of said portion of said basic plaster is made of transparent material, preferably polyethylene or polypropylene.

Thus, the official person can check the freedom from damage of the attachment system without removing it.

In another preferred embodiment, said hollow space 5 formed between said basic and detection plasters contains a dye, solid matter or odor marker which is meant to serve as proof for unauthorised removal.

The size of said hollow space 5 is variable in accordance with the recess in said supporting material 4*a* of said detection plaster. If said hollow space 5 contains a dye solution as marker, a very small size is sufficient. When removing the attachment device from the body, said hollow space 5 is torn open so that the emerging dye material will change the color of the surrounding supporting material (e.g., a fabric) and/or the skin area located beneath. According to the present invention, leuco dyes are preferably used as markers in said hollow space 5, e.g. leuco malachite green or leuco crystal purple (supplier: Messrs. Aldrich).

If the sensor is removed by an official person, a change of color on the skin and/or the plaster indicates that the sensor has been removed before. If the dye solution is set free at this moment, however, the sensor has not been removed before.

In another embodiment of the present invention according to patent claim 5, said hollow space 5 may also be marked by a solid matter having a characteristic color and/or a solid matter having a characteristic spatial structure the missing of which would indicate an unauthorised removal of the attachment device. In this case, preferably polyethylene granulate or colored lead glass beads are used. According to the present invention, preferably such solid materials are used which are not available to average people in order to prevent abuse by refilling and re-attachment.

In another embodiment of the present invention, said hollow space 5 of the attachment device may also contain an odor marker using an odorized matter or a gas having a characteristic odor (such as hydrogen sulphide) so that the missing of said characteristic odor during the removal of the sensor by the official person would indicate its unauthorised prior removal.

The present invention is described in more detail using the example embodiments below.

EXAMPLE 1

An annular plaster 3 having an outer diameter of 8 cm and an inner diameter of 3.5 cm, which is used for attaching a sensor having the size of a wrist watch, contains in an integrated state, i.e. by adhering a detection plaster 4 having a diameter of 1 cm during the manufacturing process, a flat circular capsule having an inner height of 1 mm and an inner diameter of 5 mm which, during removal of said annular plaster 3 from the skin is forcedly opened due to the fact that only said detection plaster 4 remains sticking to the skin. Thus, some drops of a dye fluid having been injected into the capsule during the manufacturing process, e.g. a 10 percent aqueous eosin solution, are set free. The dye matter changes the color of the surrounding plaster and the skin. Said detection plaster 4 which continues to stick to the skin is then peeled off (by the official person) in the same way as said basic plaster 3 before.

EXAMPLE 2

The procedure is similar to that described in example 1, but leuco malachite green is used as leuco dye. In this variant according to the present invention, the skin will only change its color after oxygen access.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for attaching a sensor to the surface of the skin so as to fix the sensor to the skin, the device comprising:
   a basic plaster having a supporting layer and an adhesive layer; and
   a detection plaster having a supporting layer, a recess being provided in the supporting layer of the detection plaster, the supporting layer of the detection plaster being attachable to the adhesive layer of the basic plaster to provide a hollow space therebetween, the recess being a part of the hollow space, an adhesion strength between the supporting layer of said detection plaster and the adhesive layer of the basic plaster being less than
   an adhesion strength between the basic plaster and the skin and
   an adhesion strength between the detection plaster and the skin.

2. The attachment device according to claim 1, wherein a portion of the basic plaster covering the hollow space is without the adhesive layer, the supporting layer of the basic plaster adjacent the portion without the adhesive layer is formed of a transparent material.

3. The attachment device according to claim 2, wherein the transparent material is one of polyethylene or polypropylene.

4. The attachment device according to claim 1, wherein the hollow space contains at least one of a dye solution, a solid matter, an odorized substance or a gas.

5. The attachment device according to claim 1, wherein the hollow space contains a leuco dye.

6. The attachment device according to claim 1, wherein the hollow space contains a solid matter with at least one of a characteristic color and spatial structure.

7. The attachment device according to claim 1, wherein the hollow space contains a gas having a characteristic odor.

8. The attachment device according to claim 1, wherein the adhesion strength of both the basic plaster and the detection plaster with the skin is the same.

9. The attachment device according to claim 1, wherein the adhesion strength of the detection plaster to the skin is greater than the adhesion strength of the basic plaster to the skin.

10. A method for proving removal of the sensor from the surface of the skin using the attachment device according to claim 1, comprising the step of during the removal of a sensor which is attached to the skin by the attachment device, the basic plaster is peeled off of the skin while the detection plaster remains on the skin with an adhesive layer of the detection plaster thereby causing the hollow space to tear open and to thereby prove removal of the sensor.

11. The method according to claim 10 wherein proof of removal includes use of at least one of a dye solution, a solid matter, an odorized substance and a gas which is present inside the hollow space and which escapes from the hollow space during the removal of the sensor from the skin.

12. A method for proving removal of a sensor from skin, the method comprising the steps of:
   fixing the sensor to the skin, the sensor being fixed by an attachment device, the attachment device including a basic plaster having a supporting layer and an adhesive layer, and the attachment device further including a detection plaster having a supporting layer and an adhesive layer, a recess being provided in the supporting layer of the detection plaster;
   adhering the basic plaster on the skin and adhering the detection plaster on the skin during the step of fixing;
   attaching the supporting layer of the detection plaster to the adhesive layer of the basic plaster to form a hollow space therebetween, the recess being a part of the hollow space;
   providing adhesion strength between the supporting layer of the detection plaster and the adhesive layer of the basic plaster to be less than adhesion strength between the basic plaster and the skin and less than adhesion strength between the detection plaster and the skin;
   peeling the basic plaster from the skin while the detection plaster remains on the skin with its adhesive layer during the removal of the sensor; and
   tearing open the hollow space during the step of peeling in order to prove removal of the sensor.

13. The method according to claim 12, further comprising the use of at least one of a dye solution, a solid matter, an odorized substance and a gas which is present inside the hollow space and which escapes from the hollow space during the removal of the sensor from the skin.

* * * * *